(12) United States Patent
Kourtakis et al.

(10) Patent No.: US 6,500,779 B2
(45) Date of Patent: Dec. 31, 2002

(54) MOLYBDENUM BASED OXIDATION CATALYSTS

(75) Inventors: Kostantinos Kourtakis, Swedesboro, NJ (US); John Donal Sullivan, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/878,645

(22) Filed: Jun. 11, 2001

(65) Prior Publication Data

US 2002/0049136 A1 Apr. 25, 2002

Related U.S. Application Data

(62) Division of application No. 09/269,211, filed as application No. PCT/US97/16563 on Sep. 18, 1997, now Pat. No. 6,271,169.
(60) Provisional application No. 60/026,597, filed on Sep. 24, 1996.

(51) Int. Cl.$^7$ ............. B01J 23/24; B01J 23/26; B01J 23/10; B01J 23/02; B01J 23/74
(52) U.S. Cl. ............. 502/305; 502/303; 502/306; 502/311; 423/21.1; 423/49; 423/53; 423/61; 423/62; 423/69; 423/89; 423/111; 423/179; 423/155; 423/138; 423/179.5
(58) Field of Search ................. 502/303, 305, 502/306, 311; 423/21.1, 49, 53, 61, 62, 69, 89, 111, 179, 155, 138, 179.5

(56) References Cited

U.S. PATENT DOCUMENTS

| | | | |
|---|---|---|---|
| 2,625,519 A | | 1/1953 | Hartig |
| 3,928,392 A | | 12/1975 | Cherry et al. |
| 3,968,054 A | | 7/1976 | Cherry et al. |
| 4,065,468 A | | 12/1977 | Grasselli et al. |
| 4,192,951 A | | 3/1980 | Slinkard et al. |
| 4,668,802 A | | 5/1987 | Contractor |
| 5,055,441 A | * | 10/1991 | McCarron, III et al. .... 502/321 |

FOREIGN PATENT DOCUMENTS

EP 0052839 6/1982

OTHER PUBLICATIONS

Zazhigalov, V. A. et al., Oxidation of n–butane on Vanadium Molybdenum–Oxide Catalysts, Inst. Fiz. Khim. im. Pisarzhevskogo, Kiev USSR Neftekhimiya, 17(2), 266–73, 1977, No Month.

Mazzochia, C. R. et al., Selective Oxidation of Butane in the Presence of NiOMoO3 catalysts, An. Quim.Ser.A79, No. 1, 108–113, 1983, No Month.

Ozkan, Umit & Schrader, G. L., Synthesis, Characterization and catalytic behaviour of cobalt molybdates for 1–butene oxidation to maleic anhydride, Applied Catalysis, 23, 327–338, 1986, No Month.

Parausanu, Victor et al., Selective Oxidation of Pure C4 Hydrocarbons with the V2O5–MoO3 Catalytic System, Rev. Chim. Bucharest 43, No. 10, 609–13, 1992, No Month.

Fumagalli, C. et al., Facile and not facile reactions for the production of maleic and phthalic anhydrides with vanadium mixed oxides based catalysts, Catalysis Letters 21, 19–26, 1993, No Month.

Ozkan, Umit S. et al., Synergy Effects in Selective Oxidation Catalysis, Studies in Surface Science and Catalysis, vol. 72, 363–377, 1992, No Month.

Jung, J. S. et al., Co–Mo–O–Ti, A New Catalyst Effective in Butane Oxidation to Maleic Anhydride, Adsorption and Catalysis on Oxide Surfaces, 345–354, 1985, No Month.

Portela, M. F. et al., Catalytic activity of unpromoted and promoted nickel molybdate in butane selective oxidation, Chem. Commun., 501–502, 1996, No Month.

* cited by examiner

Primary Examiner—Elizabeth D. Wood

(57) ABSTRACT

This invention concerns catalysts comprising a molybdenum compound of formula I, II, III, IV or V I $V_qMoA_yO_z$ II $NiMo_xB_yO_{z'}$ III $VNi_wMo_xC_yO_{z''}$ IV $CoNi_wMo_xD_yO_{z'''}$ V $VNi_wCo_rMo_xE_yO_{z''''}$ wherein: A is at least one cation selected from the group consisting of cations of: Cr, Sb, Co, Ce and Pb; B is at least one cation selected from the group consisting of cations of: Sb, Al and W; C is at least one cation selected from the group consisting of cations of: Fe, Zn, Al, Sb, Bi, W, Li, Ba, Nb and Sn; D is at least one cation selected from the group consisting of cations of: Ba, Mn, Al, Sb, Sn, and W; E is at least one cation selected from the group consisting of cations of: Fe, Ca, Mn, Sr, Eu, La, Zr, Ga, Sn and Pb; q, r, w, x and y are each independently a number from 0.1 to 10 and y' is a number from 0 to 10, z, z', z'', z''', and z'''' are determined using the amounts and oxidation states of all cations present in each formula. These catalysts can be used in $C_4$ oxidation processes, especially butane oxidation processes.

1 Claim, No Drawings

MOLYBDENUM BASED OXIDATION CATALYSTS

CROSS REFERENCE TO RELATED APPLICATIONS

This application is a divisional of application Ser. No. 09/269,211, filed Mar. 22, 1999 now U.S. Pat. No. 6,271,169, which is a national phase filing under 35 U.S.C. 371 of International Application Number PCT/US97/16563, filed Sep. 18, 1997, which claims priority benefit from Provisional Application No. 60/026,597, filed Sep. 24, 1996.

FIELD OF THE INVENTION

This invention relates to compounds comprising molybdenum, oxygen and certain cations, and the use of these compounds as catalysts in $C_4$ oxidation processes, especially butane oxidation processes.

TECHNICAL BACKGROUND

Oxidative organic processes are widely used in industrial operations. One commercially valuable process involves the oxidation of butane to maleic anhydride. Maleic anhydride is used as a raw material for products ranging from agricultural chemicals, paints, paper sizing and food additives to synthetic resins. To fill the high demand for this valuable chemical, a variety of commercial processes have been developed.

One important route to maleic anhydride involves the vapor phase oxidation of n-butane over a vanadium/phosphorus oxide (VPO) catalyst. The reaction step involves oxidation of n-butane with air (oxygen) to form maleic anhydride, carbon oxides, water and smaller amounts of partially oxidized by-products. Typically, the process is carried out in fixed-bed reactors, fluid-bed reactors, or more recently in recirculating solids reactors having two reaction zones in which two separate reactions take place with a catalyst (the solid) circulating between the two reaction zones and taking part in reactions in both zones.

A number of non-VPO catalysts have been reported in the literature. Zazhigalov, V. A. et al., in an article entitled "Oxidation of n-butane on Vanadium Molybdenum-Oxide Catalysts", Inst. Fiz. Khim. im. Pisarzhevskogo, Kiev USSR Neftekhimiya (1977), 17 (2),268–73 describe the activity of $V_2O_5$-$MoO_3$ catalysts in butane oxidation as passing through a maximum at 25% $MoO_3$, and that a certain catalytic structure consisting of, $V^{4+}$, $V^{5+}$ and $Mo^{6+}$ ions correspond to their preferred catalyst composition. These results obtained at 500–600° C. indicate low catalyst activity at normal operating temperatures.

Mazzochia, C. R. et al., in "Selective Oxidation of Butane in the Presence of NiO-$MoO_3$ catalysts"; An. Quim. Ser. A 79, no. 1 108–113(1983) disclose nickel molybdate catalysts prepared by coprecipitation that exhibit low hydrocarbon conversions. At 475° C., 19% conversion of n-butane was noted with low selectivities to maleic anhydride.

Umit Ozkan and G. L. Schrader, in "Synthesis, Characterization and catalytic behaviour of cobalt molybdates for 1-butene oxidation to maleic anhydride", Applied Catalysis, 23 (1986) 327–338 disclose the use of cobalt molybdate for the oxidation of 1-butene.

In spite of the progress in catalyst and process development over the years, a need still remains for improved non-VPO catalysts useful in the oxidation of C4 hydrocarbons, particularly n-butane, to maleic anhydride and especially catalysts which are active at lower temperatures and have shorter contact times; and it is to that end that the present invention is directed.

SUMMARY OF THE INVENTION

The present invention provides a catalyst, comprising a molybdenum compound of formula I, II, III, IV or V:

I $V_qMoA_yO_z$

II $NiMo_xB_yO_{z'}$

III $VNi_wMo_xC_yO_{z''}$

IV $CoNi_wMo_xD_yO_{z'''}$

V $VNi_wCo_rMo_xE_yO_{z''''}$ wherein:

q is a number from 0.1 to 10;
r is a number from 0.1 to 10;
w is a number from 0.1 to 10;
x is a number from 0.1 to 10;
y is a number from 0.1 to 10;
y is a number from 0 to 10, A is at least one cation selected from the group consisting of cations of: Cr, Sb, Co, Ce and Pb;

B is at least one cation selected from the group consisting of cations of: Sb, Al and W;

C is at least one cation selected from the group consisting of cations of: Fe, Zn, Al, Sb, Bi, W, Li, Ba, Nb and Sn;

D is at least one cation selected from the group consisting of cations of: Ba, Mn, Al, Sb, Sn, and W;

E is at least one cation selected from the group consisting of cations of: Fe, Ca, Mn, Sr, Eu, La, Zr, Ga, Sn and Pb; and z, z', z", z'", and z"" are determined using the amounts and oxidation states of all cations present in each formula according to the following equations:

z=((q times oxidation state of V)+(1 times oxidation state of Mo)+(y times oxidation state of A)) divided by 2 (oxidation state of oxygen);

z'=((1 times oxidation state of Ni)+(x times oxidation state of Mo)+(y times oxidation state of B)) divided by 2 (oxidation state of oxygen);

z"=((1 times oxidation state of V)+(w times the oxidation state of Ni)+(x times oxidation state of Mo)+(y' times oxidation state of C)) divided by 2 (oxidation state of oxygen);

z'"=((1 times oxidation state of Co)+(w times the oxidation state of Ni)+(x times oxidation state of Mo)+(y' times oxidation state of D)) divided by 2 (oxidation state of oxygen); and z""=((1 times oxidation state of V)+(w times the oxidation state of Ni)+(r times the oxidation state of Co)+(x times oxidation state of Mo)+(y' times oxidation state of E)) divided by 2 (oxidation state of oxygen).

The present invention also provides a process for the oxidation of a C4 hydrocarbon to maleic anhydride, comprising: contacting the C4 hydrocarbon with a source of oxygen in the presence of a catalytic amount of a molybdenum catalyst comprising a compound of formula I, II, III or V, as defined above, to yield maleic anhydride.

The present invention further provides a process for the oxidation of n-butane to maleic anhydride, comprising: contacting n-butane with a source of oxygen in the presence of a catalytic amount of a molybdenum catalyst comprising a compound of formula IV, as defined above, wherein the molybdenum catalyst is in a bulk state, to yield maleic anhydride.

The present invention also provides a process for the oxidation of n-butane to maleic anhydride, comprising: contacting n-butane with a source of oxygen in the presence of a catalytic amount of a catalyst comprising a molybdenum compound of formula VI or VII in a crystalline, active phase VI $V_9Mo_6O_{40}$ VII $V_2MoO_8$ to yield maleic anhydride.

The present invention also provides a process for the preparation of a molybdenum compound comprising a crystalline oxide of formula I, II, III, IV or V, as described above, comprising the steps of: contacting at least one compound having a cation of the molybdenum compound with at least one cation containing compound for each of the other cations of the molybdenum compound in a solution comprising water to form a resultant solution or colloid; freezing the resultant solution or colloid to form a frozen material, freeze drying the frozen material; and heating the dried frozen material to yield the molybdenum compound of formula I, II, III, IV, V, VI or VII.

DETAILED DESCRIPTION OF THE INVENTION

Multicomponent catalyst systems have been identified herein wherein the presence of molybdenum in combination with other particular cations show a significant beneficial effect on catalyst performances compared with many non-VPO catalysts reported in the literature for n-butane oxidation. These new multicomponent catalysts of the present invention comprise a molybdenum compound of formula I, II, III, IV or V:

I $V_qMoA_yO_z$

II $NiMo_xB_yO_{z'}$

III $VNi_wMo_xC_yO_{z''}$

IV $CoNi_wMo_xD_yO_{z'''}$

V $VNi_wCo_vMo_xE_yO_{z''''}$ wherein: q is a number from 0.1 to 10; r is a number from 0.1 to 10; w is a number from 0.1 to 10; x is a number from 0.1 to 10; y is a number from 0.1 to 10; and y' is a number from 0 to 10.

A is at least one cation selected from the group consisting of cations of: Cr, Sb, Co, Ce and Pb. A is preferably Sb, and a preferred compound of formula I is $V_1Mo_1Sb_1O_z$. B is at least one cation selected from the group consisting of cations of: Sb, Al and W. B is preferably Sb, and a preferred compound of formula II is $Ni_1Mo_{2.3}Sb_1O_{z'}$. C is at least one cation selected from the group consisting of cations of: Fe, Zn, Al, Sb, Bi, W, Li, Ba, Nb and Sn. C is preferably Bi, or Nb and Sn, and preferred compounds of formula III are $V_1Mo_{2.3}Ni_1Bi_1O_{z''}$, and $V_1Mo_{2.3}Ni_1Nb_1Sn_1O_{z''}$. D is at least one cation selected from the group consisting of cations of: Ba, Mn, Mo, Al, Sb, Sn, and W. D is preferably Sn or W, and preferred compounds of formula IV are $Co_{0.5}Ni_{0.5}Mo_3Sn_{0.5}O_{z'''}$ and $Mo_3Co_{0.5}Ni_{0.5}W_1O_{z'''}$. E is at least one cation selected from the group consisting of cations of: Fe, Ca, Mn, Sr, Eu, La, Zr, Ga, Sn and Pb. E is preferably Fe, Sr, Zr, Ga or Pb, and preferred compounds of formula V are $V_1Mo_{2.3}Ni_{0.5}Co_{0.5}Fe_1O_{z''''}$, $V_1Mo_{2.3}Co_{0.5}Ni_{0.5}Sr_1O_{z''''}$, $V_1Mo_{2.3}Co_{0.5}Ni_{0.5}Zr_1O_{z''''}$, $V_1Mo_{2.3}Co_{0.5}Ni_{0.5}Ga_1O_{z''''}$ and $V_1Mo_{2.3}Co_{0.5}Ni_{0.5}Pb_1O_{z''''}$.

The ranges for z, z', z", z''', and z"" defining the subscript for oxygen in the formulae I–V, varies widely. The value of z, z', z", z''', and z"" is defined using the range of possible oxidation states of all of the cations found in the molybdenum compound as shown below.

For the molybdenum compounds of formula I, the highest oxidation states of the A cations are: $V^{5+}$, $Mo^{6+}$, $Cr^{6+}$, $Sb^{5+}$, $Co^{3+}$, $Ce^{4+}$ and $Pb^{4+}$; and the lowest oxidation states for the A cations are: $V^{3+}$, $Mo^{4+}$, $Cr^{2+}$, $Sb^{3+}$, $Co^{2+}$, $Ce^{3+}$ and $Pb^{2+}$. Therefore, for example, when the molybdenum compound of formula I is $V_{10}Mo_1A_{10})_z$, wherein A is Cr, the maximum value for z. $z_{max}$, is: $z_{max}=((10\times5)+(1\times6)+(10\times6))\div by\ 2=116/2=58$. The minimum value for z, $z_{min}$, in formula I wherein A is Cr is: $z_{min}=((10\times3)+(1\times4)+(10\times2))\div by\ 2=54/2=27$. When the molybdenum compound of formula I is $V_{0.1}Mo_1A_{0.1}O_z$, wherein A is Pb, $z_{max}=((0.1\times5)+(1\times6)+(0.1\times4))\div by\ 2=6.9/2=3.45$. The minimum value for z, $z_{min}$, in formula I wherein A is Pb is: $z_{min}=((0.1\times3)+(1\times4)+(0.1\times2))\div by\ 2=4.5/2=2.25$. Thus, for molybdenum compounds of formula I, z ranges from 2.25 to 58.

For molybdenum compounds of formula II, the highest oxidation states are: $Ni^{3+}$, $Mo^{6+}$, $Sb^{5+}$, $Al^{3+}$, and $W^{6+}$ and the lowest oxidation states are: $Ni^{2+}$, $Mo^{2+}$, $Sb^{3+}$, $Al^{3+}$, and $W^{2+}$. $z'_{max}$ and $z'_{min}$ can be calculated as shown above for $z_{max}$ and $z_{min}$ of formula I.

For molybdenum compounds of formula III, the highest oxidation states are, $V^{5+}$, $Ni^{3+}$, $Mo^{6+}$, $Fe^{3+}$, $Zn^{2+}$, $Al^{3+}$, $Sb^{5+}$, $Bi^{5+}$, $W^{6+}$, $Li^{1+}$, $Ba^{2+}$, $Nb^{5+}$, and $Sn^{4+}$, and the lowest oxidation states are: $V^{2+}$, $Ni^{2+}$, $Mo^{2+}$, $Fe^{2+}$, $Zn^{2+}$, $Al^{3+}$, $Sb^{3+}$, $Bi^{3+}$, $W^{2+}$, $Li^{1+}$, $Ba^{2+}$, $Nb^{3+}$, and $Sn^{2+}$. $z''_{max}$ and $z''_{min}$ can be calculated as shown above for $z_{max}$ and $z_{min}$ of formula I. Since there can be mixtures of the C cations, these must be factored into the ranges for z.

For molybdenum compounds of formula IV, the highest oxidation states are: $Co^{3+}$, $Ni^{3+}$, $Mo^{6+}$, $Ba^{2+}$, $Mn^{7+}$, $Al^{3+}$, $Sb^{5+}$, $Sn^{4+}$, and $W^{6+}$, and the lowest oxidation states are: $Co^{2+}$, $Ni^{2+}$, $Mo^{2+}$, $Ba^{2+}$, $Mn^{2+}$, $Al^{3+}$, $Sb^{3+}$, $Sn^{2+}$, and $W^{2+}$. $z'''_{max}$ and $z'''_{min}$ can be calculated as shown above for $z_{max}$ and $z_{min}$ of formula I.

For molydbenum compounds of formula V, the highest oxidation states are: $V^{5+}$, $Ni^{3+}$, $Co^{3+}$, $Mo^{6+}$, $Fe^{3+}$, $Ca^{2+}$, $Mn^{7+}$, $Sr^{2+}$, $Eu^{3+}$, $La^{3+}$, $Zr^{4'}$, $Ga^{3+}$, $Sn^{4+}$ and $Pb^{4+}$, and the lowest oxidation states are: $V^{2+}$, $Ni^{2+}$, $Co^{2+}$, $Mo^{2+}$, $Fe^{2+}$, $Ca^{2+}$, $Mn^{2+}$, $Sr^{2+}$, $Eu^{2+}$, $La^{3+}$, $Zr^{4+}$, $Ga^{3+}$, $Sn^{2+}$ and $Pb^{2+}$. $z''''_{max}$ and $z''''_{min}$ can be calculated as shown above for $z_{max}$ and $z_{min}$ of formula I.

The catalysts of the present invention can be either a particular structure (containing a certain ratio of cations) or a combination of structures and thus comprise a mixture of the crystalline oxides of the molybdenum compound of formula I, II, III, IV or V and may further comprise the amorphous phase of the compound.

The molybdenum compounds of the present invention can be prepared by various methods, for example, by freeze drying. alcohol reflux and gel techniques. Spray roasting, spray drying and coprecipitation could also be employed. Ceramic methods, i.e., solid state techniques could be used but are, in general, less preferred. Certain compounds of formulas I–V are better prepared by one method over another as appreciated by one of ordinary skill in the art.

The catalyst preparative process is usually conducted at normal atmospheric pressure, but elevated or reduced pressures can be employed. Agitation is not required, but is usually provided to facilitate a homogeneous mix and to facilitate heat transfer.

One process for the preparation of a catalyst comprising a molybdenum compound of formulas I, II, III, IV, V, VI or VII, as described above, comprises contacting at least one cation containing compound with at least one cation containing compound for each of the other cations of the final molybdenum compound in a solution comprising water to form a resultant solution or colloid; freezing the resultant solution or colloid to form a frozen material; freeze drying the frozen material; and heating the dried frozen material to yield the molybdenum compound of formula I, II, III, IV, V, VI or VII.

The compound containing a cation of the final molybdenum compound of formula I, II, III, IV, V, VI or VII can be a salt, oxide or the like. The cation containing compounds are contacted with each other upon their addition to the solution comprising water. There is at least one cation containing compound for each of the cations in the molybdenum compound of formula I, II, III, IV, V, VI or VII. Each cation can be contained in a separate cation containing compound or more than one cation can be contained in the same cation containing compound. There can also be more than one cation containing compound for each cation in the final molybdenum compound of formulas I, II, III, IV. V, VI or VII. The cation containing compounds can be ammonium or sodium salts of molybdic acid, vanadic acid or tungstic acid, in addition to compounds containing the A, B, C, D, E cation of choice or other cations present in the final molybdenum compound of formulas I, II, III, IV, V, VI or VII. For example, the oxides or acetylacetonates, chlorides or acetates of Li, Cr, Mn, Mo. Fe, Co, Ni, Ce, W, Zn, Sr, Nb, Eu, Ba, Zr, Al, Ca, Sn, Pb, Sb, Bi, La and Ga can be cation containing compounds. Representative examples of such salts or oxides containing cations of the final molybdenum compound of formula I, II, III, IV, V, VI or VII can be found in Tables 1–6 of the present invention. Normal commercially available reagents can be used for the cation containing compounds used in the preparation of the molybdenum compound. The highest purity products attainable need not be employed, however the purity of the reagents must be known in order to calculate the gross amount required. In addition the reagents should not be contaminated with any catalyst poison. The amount of reagent employed should be within plus or minus 5%, preferably within plus or minus 2% of the amount indicated by stoichiometry.

The cation containing compounds are dissolved in an appropriate solvent to form a solution or fine colloid. The formation of a solution, as opposed to a colloid, is generally preferred for most effective mixing.

In cases where $NH_4VO_3$ is the cation containing compound used, $NH_4VO_3$ salt can be dissolved in water prior to adding the other cation containing compounds by heating water or other appropriate solvents. The additional cation containing compounds can then be added to form a resultant solution or a finely mixed colloid. The resultant solution or colloid is rapidly frozen at liquid nitrogen temperatures. Rapid freezing ensures the cation containing compounds will remain intimately mixed and will not segregate to any significant degree. The frozen material can then be transferred to a freeze drier, such as a Virtis Freeze Drier (Baltimore, Maryland) equipped with a Unitop unit. The solution is kept frozen while water vapor is removed by evacuation. In order to prevent melting of the frozen material, the freeze drier can be maintained at a temperature ranging from about 0° C. to about –40° C., preferably between –40° C. to –20° C. with a vacuum of 2–10 millitorr. After at least 24 hours, preferably about 2–4 days, the dried sample can be calcined (heated) in air at a temperature ranging from about 250° C. to about 500° C., preferably about 400° C., for a time sufficient to decompose the cation containing compounds of formula I, II, III, IV, V, VI or VII to form metal oxide phases. This will require heating for a period of about 0.5 hours to about 24 hours.

Freeze drying methods can produce mixtures of solid cation containing compounds which are nearly as well mixed as their solution counterparts. The method is superior to slower solvent evaporation because homogeneity can be lost during the removal of solvent. In addition, in many cases because the cation containing compounds are well mixed, a lower calcination temperature can be used, and can allow for the synthesis of metal oxides with higher surface areas than typically observed by traditional high temperature ceramic syntheses. Choice of calcination temperature and protocols and atmosphere can also influence the types of phases synthesized.

Another process for the preparation of a catalyst comprising a molybdenum compound of formula I, II, III, IV, V, VI or VII, as described above, comprises the steps of: mixing a solution comprising at least one cation containing compound for each of the cations in the molybdenum compound of formula I, II, III, IV, V, VI, VI or VII and an alcohol to form a suspension; heating the suspension to reflux; and isolating the molybdenum compound of formula I, II, III, IV, V, VI or VII.

At least one cation containing compound for each of the cations in the molybdenum compound of formula I, II, III, IV, V, VI or VII are combined with an alcohol or combination of alcohols, such as ethyl alcohol, ethyl alcohol/benzyl alcohol mixtures, 1-propanol, 1-butanol, isobutyl alcohol, 2-methyl-2 propanol, 1-heptanol, neopentyl alcohol, phenol or the like, to form a suspension. The cation containing compounds can be those as described above for the freeze drying process. Mixing or agitation can be supplied via methods known in the art. The preparation can be carried out in a dry box to prevent any hydration. The resulting suspension is next heated to reflux under an inert atmosphere, such as nitrogen, for a time sufficient to ensure a proper solution. After the solution is formed, the solvent can be removed by freeze drying, rotary-evaporation, or a slow drying process after filtering, decanting or the like. The dried material can then be calcined at a temperature ranging from about 250° C. to about 500° C., preferably about 400° C., under air for a time sufficient to form the molybdenum compound of formula I, II, III, IV, V, VI or VII. This can take from about 0.5 hours to about 24 hours.

A further process for the preparation of a catalyst comprising a molybdenum compound of formula I, II, III, IV, V, VI or VII, as described above, comprises the steps of: contacting at least one cation containing compound for each cation of the molybdenum compound of formula I, II, III, IV, V, VI or VII with at least one cation containing compound for each of the other cations in the molybdenum compound of formula I, II, III, IV, V, VI or VII in a solution comprising water to form a resultant solution or colloid; stirring the resultant solution or colloid until gelation occurs; and drying the gel to yield the molybdenum compound of formula I, II, III, IV, V, VI or VII.

The cation containing compounds for this gel process can be those as described above for the freeze drying process. Following contact of the cation containing compounds with each other, the resultant solution or colloid is stirred until gelation occurs. In some cases an adjustment of pH is needed to induce gelation. Acid or base can be added depending on the nature of the other ingredients being used in the preparation of the molybdenum compound. Gelation can occur at room temperature at atmospheric pressure. The resulting gel can be dried and then calcined at a temperature ranging from about 250° C. to about 450° C., preferably 400° C., under air for a time sufficient to thoroughly dry.

Compounds of formula I, II, III, and V of the present invention are useful as catalysts in the oxidation of C4 hydrocarbons. The present invention provides a process for the oxidation of C4 hydrocarbons to maleic anhydride, comprising: contacting the C4 hydrocarbon with a source of oxygen in the presence of a catalytic amount of a catalyst comprising a molybdenum compound of formula I, II, III or V as defined above. The C4 hydrocarbon is selected from the group consisting of: n-butane, 1-butene, 2-butene and butadiene, and isomers thereof.

In some instances the catalyst may be useful as a lattice oxygen catalyst in the oxidation of C4 hydrocarbons with the ability to selectively oxidize the C4 hydrocarbon in the absence of gas phase oxygen and thus can be the only source of oxygen.

The catalyst comprising the molybdenum compound of formula I, II, III or V can be used alone, supported on a catalyst support or impregnated in a carrier material. Typical support carrier materials are well known to those skilled in the art as are methods of preparing supported or impregnated catalysts. Typical materials comprise silica, titania, zirconia, alumina, thoria, silicon carbide and carbon. The catalyst comprising the molybdenum compound described herein can be used as isolated, or in cases where size and shape of the catalyst is dictated by the requirements of the equipment employed in the subsequent use of the catalyst, the catalyst can be processed or fabricated into various size and shape particles before use by grounding, pelletizing, briquetting, tabulating, or shaping in other ways as required.

A first group of compounds, listed in Table 1 as Examples 1–5, are of formula I: $V_qMoA_yO_z$, where q varies from 0.1 to 10, y varies from 0.1 to 10, A is at least one cation selected from the group consisting of cations of Cr, Sb, Co, Ce and Pb, and z is calculated as above. The performance of these molybdenum compounds as catalysts in the oxidation of n-butane is shown in Table 1.

A second group of compounds, listed in Table 2 as Examples 6–9, are of formula II: $NiMo_xB_yO_{z'}$, where x varies from 0.1 to 10, y varies from 0.1 to 10, B is at least one cation selected from the group consisting of cations of Sb, Al and W and z' is calculated as above. The performance of these molybdenum compounds as catalysts in the oxidation of n-butane is shown in Table 2.

A third group of compounds, listed in Table 3 as Examples 10–21, are of formula III: $VNi_wMo_xC_yO_{z''}$, where w varies from 0.1 to 10, x varies from 0.1 to 10, y' varies from 0 to 10, C is at least one cation selected from the group consisting of cations of Fe, Zn, Al, Sb. Bi, W, Li, Ba, Nb and Sn and z'' is calculated as above. The performance of these molybdenum compounds as catalysts in the oxidation of n-butane is shown in Table 3.

Another group of compounds, listed in Table 5 as Examples 27–35, are of formula V: $VNi_wCo_rMo_xE_yO_{z'''}$, where w varies from 0.1 to 10, r varies from 0.1 to 10, x varies from 0.1 to 10, y varies from 0.1 to 10, E is at least one cation selected from the group consisting of cations of Fe, Ca, Mn, Sr, Eu, La, Zr, Ga, Sn and Pb and z'''' is calculated as above. The performance of these molybdenum compounds as catalysts in the oxidation of n-butane is shown in Table 5.

The present invention further provides a process for the oxidation of n-butane to maleic anhydride comprising contacting n-butane with a source of oxygen in the presence of a catalytic amount of a catalyst comprising a molybdenum compound of formula IV, as defined above, in a bulk state.

In some instances the catalysts comprising a molybdenum compound of formula IV of the present invention are used as catalysts in the bulk state, i.e., not on a support, but as pure compounds. The catalyst comprising the molybdenum compound of formula IV may be the only source of oxygen. The catalytic oxidation can be carried out in a fixed or fluidized bed reactor.

A group of compounds, listed in Table 4 as Examples 22–26, are of formula IV: $CoNi_wMo_xD_yO_{z'''}$, where w varies from 0.1 to 10, x varies from 0.1 to 10, y varies from 0.1 to 10, D is at least one cation selected from the group consisting of cations of Ba, Mn, Al, Sb, Sn and W, and z''' is calculated as above. The performance of these molybdenum compounds as catalysts in the oxidation of n-butane is shown in Table 4.

The present invention also provides a process for the oxidation of n-butane to maleic anhydride, comprising: contacting n-butane with a source of oxygen in the presence of a catalytic amount of a catalyst comprising a molybdenum compound of formula VI or VII in a crystalline, active phase VI $V_9Mo_6O_{40}$ VII $V_2MoO_8$ to yield maleic anhydride. Prepared as herein described, the molybdenum compound of formula VI or VII is formed with little $MoO_3$ by-product. The performance of this molybdenum compound in a crystalline, active phase as a catalyst in oxidation of n-butane is shown in Example 36 of Table 6.

Comparative Examples 37–41, not of this invention, and the performance of these materials as catalysts in the oxidation of n-butane is listed in Table 7.

Prior to use in the microreactor, the catalysts described herein are typically formed into a convenient catalyst shape by pelletizing the catalyst at about 30,000 psi ($2.07 \times 10^6$ kPa) or less, to form small disks and crushing the pellet through sieves. For fixed bed reactor evaluations, typically a −40, +60 mesh is used (U.S. Sieve Series). Optionally, one could blend the resultant powder with 1–3% of a die lubricant and pellet binder, such as graphite or Sterotex®, a hydrogenated cottonseed oil, commercially available from Capital City Products Company, Columbus. Ohio, before tabletting. For fluidized bed reactor use, the preferred size range is 20 to 150 micrometers.

Glass and stainless steel are usually employed as the material of construction for the microreactor. This is not critical as long as materials that contaminate the product with catalyst poisons are not employed.

Although processes of the invention are embodied in the following laboratory scale examples, Applicant notes that the invention can be practiced on an industrial scale by making the necessary engineering and design modifications which are customary in the art.

Catalytic oxidation using a catalyst comprising a molybdenum compound of formula I, II, III, IV, V, VI or VII can be carried out in a fixed or fluidized bed reactor or recirculating solids reactor. These catalysts can be utilized advantageously with regard to conversion and selectivity in the wide variety of conventional techniques and reactor configurations employed to conduct the vapor phase oxidation of C4 hydrocarbons to maleic anhydride. For example, the conversion can be conducted in a fixed-bed reactor, whereby the catalyst particles are maintained in a fixed position and are contacted with C4 hydrocarbon and a source of oxygen, typically molecular oxygen, both in appropriate amounts, optionally in the presence of one or more inert diluent gases, at a temperature varying between 200° C. and about 450° C., preferably between about 300° C. and about 350° C. The greatest advantages of using the catalyst of this invention are realized when the conversion of C4 hydrocarbon to maleic anhydride is carried out in a recirculating solids reactor, such as that described in U.S. Pat. No. 4,668,802. This patent discloses an improved process for the selective vapor phase oxidation of n-butane to maleic anhydride over a vanadium/phosphorus/oxygen (VPO) catalyst, whereby the amount of oxygen in the feed gas to the VPO catalyst is limited to less than the stoichiometric amount required for the total amount of n-butane converted in the process. The reduced catalyst resulting from the oxidation is separated from the gaseous product stream and is reoxidized, optionally in a separate reaction zone, before being contacted with n-butane.

The catalysts of the present invention demonstrate good results in activity, conversion and selectivity. Tables 1–6 below show conversion and selectivity after 1 sec and after 3 sec for various catalysts of the present invention and compare these results with those of other catalysts in the art (Table 7).

EXAMPLES

The reagents for the following examples are commercially available as follows: $NH_4VO_3$, $Cr_2O_3$, $(CH_3CO_2)_7Cr_3(OH)_2$, $Ce(SO_4)_2$, $Fe(NO_3)_3\text{-}9H_2O$, $NbCl_5$, $Co(NO_3)_2\text{-}6H_2O$, $(CH_3CO_2)_2Mn\text{-}4H_2O$, $V_2O_5$ and $La(NO_3)_3\text{-}5H_2O$ from Aldrich, Milwaukee, Wis.; $NH_4VO_3$, $MoO_3$, $Ni(OOCCH_3)_2\text{-}4H_2O$, $NiCl_2\text{-}6H_2O$, $H_2WO4$, $LiNO_3$ (anhydrous), $SnCl_2$, $(NH_4)_{10}W_{12}O_{41}\text{-}5H_2O$, $Co(NO_3)_2\text{-}6H_2O$, and $SnCl_2$ from Alfa, Ward Hill, Mass., $(NH_4)_6Mo_7O_{24}\text{-}4H_2O$), $Ni(NO_3)\text{-}6H_2O$, $Al(NO_3)_3\text{-}9H_2O$, $Bi(NO_3)_3\text{-}5H_2O$, $Ni(NO_3)_2\text{-}6H_2O$, $Co(NO_3)_2\text{-}6H_2O$, $Al(NO_3)_3\text{-}9H_2O$, $Ca(NO_3)_2\text{-}4H_2O$, and $Ni(NO_3)_2$, from Baker, Phillipsburg, N.J.; $Pb(NO_3)_2$, $NiCl_2\text{-}6H_2O$, $Pb(NO_3)_2$, and $H_3PO_4$ from EM Sciences, Gibbstown, N.J.; $(NH_4)_6Mo_7O_{24}\text{-}4H_2O$) from Mallinchkrodt, Erie, Pa.; $NH_4VO_3$, $Sb(OOCCH_3)_3$, $Co(OOCCH_3)_2$, $Zr(SO_4)_2\text{-}4H_2O$ and $Ga(NO_3)_3$ from J&M, Ward Hill, Mass.; colloidal $(Al_2O_3)$ from Nyacol, Ashland, Mass.; $Zn(NO_3)_2\text{-}6H_2O$ from Fisher, Fairlane, N.J.; and $Ba(NO_3)_2$ and $EuCl_2$ from AESAR, Ward Hill, Mass.

General Procedure for Freeze Drying

The component salts (indicated in the tables) were added to the indicated amount of water. In cases where $NH_4VO_3$ was used, the salt was dissolved in water prior to adding the other components by bringing the solvent to a boil. The additional salts were then added to form the solution or finely mixed colloid/slurry. The resultant solutions/colloids were rapidly frozen in glass dishes (3" diameter) using liquid nitrogen. The frozen material was then transferred to a Virtis Freeze Drier (Baltimore, Md.) equipped with a Unitop unit. In order to prevent melting of the frozen solid, the Unitop chamber shelves were maintained between –40 to –20° C. with a vacuum of 2–10 millitorr. After at least 24 hours (usually 2–4 days), the dried sample was calcined (heated) in air to 400° C. for 5 hours to produce the final catalyst product. Prior to microreactor evaluations, the material was pelletized at 20,000 psi and crumbled and screened on –40, +60 mesh screens.

General Procedure for Alcohol Reflux

Specific Preparation of $V_2MoO_8$

Vanadium pentoxide. $V_2O_5$, 90.94 g 0.500 mol, and molybdic oxide. $MoO_3$, 71.97 g, 0.500 mol were combined in an round bottomed flask equipped with an agitator with 1034 ml of isobutyl alcohol and 95 ml of benzyl. The resulting suspension was heated to reflux under a nitrogen atmosphere for 16 hours. The resulting green suspension was filtered and the isolated product dried and then calcined at 400° C. under air for 5 hours.

General Procedure for Gel Method

Specific Preparation of $NiMo_{2.3}AlO_z$ 35 ml of water was added to the colloidal alumina (20% by weight). The solid oxide and nickel acetate was added. The mixture was stirred until gelation occurred. The gel was dried then calcined at 400° C. under air for 5 hours.

Micro-Reactor Evaluation of Butane Oxidation Catalysts

The catalysts were pelletized at $1.38\times10^6$ kPa into disks and subsequently crushed and sieved through (–40, +60) mesh screens. Approximately 0.9 cc of catalyst were used for each evaluation.

The catalyst testing facility consisted of six micro-reactors which were connected to a common feed source and a common analytical gas chromatograph (GC). Each of the micro-reactors consisted of a 5.0 cm by 0.64 cm stainless steel tube which was immersed in an individual sandbath to maintain isothermal conditions. The feed composition and individual reactor flow rates were metered by commercially available mass flow controllers (Tylan Model FC-260, available from Tylan Corp., Torrance, Calif.). All exit gas lines were heated to 200° C. and connected to a multiport Valco valve for the on-line analysis of products using a commercially available GC (Hewlitt-Packard 5890 Series II, Hewlitt-Packard, Palo Alto, Calif.). A computer program controlled the Valco valve to select a reactor or feed stream to fill the 0.5 ml sample loop for injection in the GC. The GC was used to analyze for butane, maleic anhydride, acetic acid, acrylic acid, other $C_1$ to $C_4$ hydrocarbons, oxygen. carbon monoxide, carbon dioxide, nitrogen and water.

The standard testing protocol for butane oxidation catalysts was developed to measure maleic anhydride selectivities and yields under hydrocarbon-lean conditions (2% n-butane, 20% oxygen) over a range of butane conversions. Temperature was varied from 350° to 380° to 400° and back to 350° C., with three contact times (nominally 3, 1, and 0.5 s) evaluated at each temperature. The temperature was returned to 350° C. to provide information about the equilibration of the catalyst. The conversion and selectivity of two representative evaluations (at 380° C.) are reported in the tables below.

TABLE 1

| Composition $V_qMoA_yO_z$ | Example | Salt Used | Gram Mole Weight | Solvent | Method of Synthesis | 380° C., 2.0% Butane/Air | | | |
|---|---|---|---|---|---|---|---|---|---|
| | | | | | | 1 sec | | 3 sec | |
| | | | | | | Conversion % | Selectivity % | Conversion % | Selectivity % |
| $V_1Mo_1Cr_1O_z$ | 1 | $NH_4VO_3$, 50% $V_2O_5$ 50% $Cr_2O_3$ $(CH_3CO_2)_7Cr_3(OH)_2$ $(NH_4)_6Mo_7O_{24}$—$4H_2O$ $MoO_3$ | 116.98 181.90 151.99 602.32 1235.90 143.94 | 250 ml $H_2O$ | freeze-dried | 41 | 6 | 75 | 2 |
| $V_1Mo_1Sb_1O_z$ | 2 | $NH_4VO_3$ $(NH_4)_6Mo_7O_{24}$—$4H_2O$ $Sb(OOCCH_3)_3$ | 116.98 1235.90 298.88 | 250 ml $H_2O$ | freeze-dried | 75 | 7 | 99 | 2 |
| $V_1Mo_1Co_1O_z$ | 3 | $NH_4VO_3$ $(NH_4)_6Mo_7O_{24}$—$4H_2O$ $Co(OOCCH_3)_2$ | 116.98 1235.90 177.023 | 250 ml $H_2O$ | freeze-dried | 70 | 3 | 99 | 0 |
| $V_1Mo_1Ce_1O_z$ | 4 | $NH_4VO_3$ $(NH_4)_6Mo_7O_{24}$—$4H_2O$ $Ce(SO_4)_2$ | 116.965 1235.9 332.24 | 250 ml $H_2O$ | freeze-dried | 18 | 9 | 45 | 4 |
| $V_1Mo_1Pb_1O_z$ | 5 | $NH_4VO_3$ $(NH_4)_6Mo_7O_{24}$—$4H_2O$ $Pb(NO_3)_2$ | 116.965 1235.9 331.2 | 250 ml $H_2O$ | freeze-dried | 15 | 8 | 33 | 4 |

TABLE 2

| Composition $NiMo_xB_yO_{z'}$ | Example | Salt Used | Gram Mole Weight | Solvent | Method of Synthesis | 380° C., 2.0% Butane/Air | | | |
|---|---|---|---|---|---|---|---|---|---|
| | | | | | | 1 sec | | 3 sec | |
| | | | | | | Conversion % | Selectivity % | Conversion % | Selectivity % |
| $Ni_1Mo_{2.3}Sb_1O_{z'}$ | 6 | $Sb(OOCCH_3)_3$ $(NH_4)_6Mo_7O_{24}$—$4H_2O$ $Ni(OOCCH_3)_2$—$4H_2O$ | 298.88 1235.9 248.82 | 59 cc of 30% HCl | freeze-dried | 10 | 21 | 26 | 12 |
| $Ni_1Mo_{2.3}Al_1O_{z'}$ | 7 | $Ni(OOCCH_3)_2$—$4H_2O$ $(NH_4)_6Mo_7O_{24}$—$4H_2O$ colloidal $(Al_2O_3)$ 20% by wt. | 248.8212 1235.9 101.9613 | 35 ml $H_2O$ | gel | 21 | 6 | 46 | <1 |
| $Ni_1Mo_{1.3}W_1O_{z'}$ | 8 | $(NH_4)_6Mo_7O_{24}$—$4H_2O$ $NiCl_2$—$6H_2O$ $H_2WO_4$ | 1235.86 237.71 249.86 | 50 ml $H_2O$ 70 ml $NH_4OH$ | freeze-dried | 10 | 13 | 24 | 2 |
| $Ni_1Mo_1W_{1.3}O_{z'}$ | 9 | $(NH_4)_6Mo_7O_{24}$—$4H_2O$ $NiCl_2$—$6H_2O$ $H_2WO_4$ | 1235.86 237.71 249.86 | 40 ml $H_2O$ 90 ml $NH_4OH$ 25 ml $H_2O$ | freeze-dried | 10 | 11 | 35 | 0 |

TABLE 3

| Composition $VNi_wMo_xC_yO_{z''}$ | Example | Salt Used | Gram Mole Weight | Solvent | Method of Synthesis | 380° C., 2.0% Butane/Air | | | |
|---|---|---|---|---|---|---|---|---|---|
| | | | | | | 1 sec | | 3 sec | |
| | | | | | | Conversion % | Selectivity % | Conversion % | Selectivity % |
| $V_1Mo_{2.3}Ni_1O_{z''}$ | 10 | $NH_4VO_3$ $(NH_4)_6Mo_7O_{24}$—$4H_2O$ $NiCl_2$—$6H_2O$ | 116.98 1235.86 237.71 | 100 cc $H_2O$ 100 cc $H_2O$ 20 cc HCl | freeze-dried | 40 | 21 | 71 | 15 |
| $V_1Mo_{2.3}Ni_1Fe_1O_{z''}$ | 11 | $NH_4VO_3$ $(NH_4)_6Mo_7O_{24}$—$4H_2O$ $Ni(NO_3)$—$6H_2O$ $Fe(NO_3)_3$—$9H_2O$ | 116.98 1235.86 290.81 404 | 100 cc $H_2O$ 100 cc $H_2O$ 20 cc $HNO_3$ | freeze-dried | 28 | 7 | 60 | <1 |
| $V_1Mo_{2.3}Ni_1Zn_1O_{z''}$ | 12 | $NH_4VO_3$ $(NH_4)_6Mo_7O_{24}$—$4H_2O$ $Ni(NO_3)$—$6H_2O$ $Zn(NO_3)_2$—$6H_2O$ | 116.98 1235.86 290.81 297.47 | 100 cc $H_2O$ 100 cc $H_2O$ 20 cc $HNO_3$ | freeze-dried | 53 | 6 | 83 | <1 |
| $V_1Mo_{2.3}Ni_1Al_1O_{z''}$ | 13 | $NH_4VO_3$ $(NH_4)_6Mo_7O_{24}$—$4H_2O$ $Ni(NO_3)$—$6H_2O$ $Al(NO_3)_3$—$9H_2O$ | 116.98 1235.86 290.81 375.13 | 100 cc $H_2O$ 100 cc $H_2O$ 20 cc $HNO_3$ | freeze-dried | 45 | 5 | 79 | 0 |

TABLE 3-continued

| | | | | | | 380° C., 2.0% Butane/Air | | | |
| | | | | | | 1 sec | | 3 sec | |
| Composition $VNi_wMo_xC_yO_{z'''}$ | Example | Salt Used | Gram Mole Weight | Solvent | Method of Synthesis | Conversion % | Selectivity % | Conversion % | Selectivity % |
| --- | --- | --- | --- | --- | --- | --- | --- | --- | --- |
| $V_1Mo_{2.3}Ni_1Sb_1O_{z'''}$ | 14 | $NH_4VO_3$ | 116.98 | 100 cc $H_2O$ | freeze-dried | 39 | 10 | 69 | 5 |
| | | $(NH_4)_6Mo_7O_{24}$—$4H_2O$ | 1235.86 | 100 cc $H_2O$ | | | | | |
| | | $Ni(NO_3)$—$6H_2O$ | 290.81 | 15 cc $HNO_3$ | | | | | |
| | | $Sb(OOCCH_3)_3$ | 298.88 | 50 cc HCl | | | | | |
| $V_1Mo_{2.3}Ni_1Bi_1O_{z'''}$ | 15 | $NH_4VO_3$ | 116.98 | 100 cc $H_2O$ | freeze-dried | 20 | 15 | 50 | 7 |
| | | $(NH_4)_6Mo_7O_{24}$—$H_2O$ | 1235.86 | 100 cc $H_2O$ | | | | | |
| | | $Ni(NO_3)$—$6H_2O$ | 290.81 | 20 cc $HNO_3$ | | | | | |
| | | $Bi(NO_3)_3$—$5H_2O$ | 485.07 | 30 cc $HNO_3$ | | | | | |
| $V_1Mo_{2.3}Ni_1W_1O_{z'''}$ | 16 | $NH_4VO_3$ | 116.98 | 100 cc $H_2O$ | freeze-dried | 30 | 10 | 71 | 2 |
| | | $(NH_4)_6Mo_7O_{24}$—$4H_2O$ | 1235.86 | 100 cc $H_2O$ | | | | | |
| | | $Ni(NO_3)$—$6H_2O$ | 290.81 | 20 cc $HNO_3$ | | | | | |
| | | $H_2WO_4$ | 249.86 | | | | | | |
| $V_1Mo_{2.3}Ni_1Li_1O_{z'''}$ | 17 | $NH_4VO_3$ | 116.98 | 100 ml $H_2O$ | freeze-dried | 11 | 17 | 20 | 11 |
| | | $(NH_4)_6Mo_7O_{24}$—$4H_2O$ | 1235.86 | | | | | | |
| | | $NiCl_2$—$6H_2O$ | 237.71 | 15 ml HCl | | | | | |
| | | $LiNO_3$ (anhydrous) | 68.9459 | | | | | | |
| $V_1Mo_{2.3}Ni_1Ba_1O_{z'''}$ | 18 | $NH_4VO_3$ | 116.98 | 100 ml $H_2O$ | freeze-dried | 35 | 10 | 66 | 2 |
| | | $(NH_4)_6Mo_7O_{24}$—$4H_2O$ | 1235.86 | 100 ml $H_2O$ | | | | | |
| | | $Ni(NO_3)$—$6H_2O$ | 290.81 | 20 ml $HNO_3$ | | | | | |
| | | $Ba(NO_3)_2$ | 261.3398 | | | | | | |
| $V_1Mo_{2.3}Ni_1Nb_1Fe_1O_{z'''}$ | 19 | $NH_4VO_3$ | 116.98 | 100 cc $H_2O$ | freeze-dried | 30 | 3 | 60 | <1 |
| | | $(NH_4)_6Mo_7O_{24}$—$4H_2O$ | 1235.86 | 50 cc $H_2O$ | | | | | |
| | | $NiCl_2$—$6H_2O$ | 237.71 | 20 cc HCl | | | | | |
| | | $NbCl_5$ | 270.71 | 70 cc HCl | | | | | |
| | | $Fe(NO_3)_3$—$9H_2O$ | 404 | | | | | | |
| $V_1Mo_{2.3}Ni_1Nb_1Sn_1O_{z'''}$ | 20 | $NH_4VO_3$ | 116.98 | 100 ml $H_2O$ | freeze-dried | 40 | 12 | 68 | 3 |
| | | $(NH_4)_6Mo_7O_{24}$—$4H_2O$ | 1235.86 | 70 ml $H_2O$ | | | | | |
| | | $NiCl_2$—$6H_2O$ | 237.71 | 20 ml HCl | | | | | |
| | | $NbCl_5$ | 270.17 | 20 ml HCl | | | | | |
| | | $SnCl_2$ | 189.61 | 50 ml $H_2O$ | | | | | |
| $V_1Mo_{2.3}Ni_1W_1Sn_1O_{z'''}$ | 21 | $(NH_4)_{10}W_{12}O_{41}$—$5H_2O$ | 3132.64 | 140 ml $NH_4OH$ | freeze-dried | 25 | 10 | 47 | 3 |
| | | $(NH_4)_5Mo_7O_{24}$—$4H_2O$ | 1235.86 | | | | | | |
| | | $NH_4VO_3$ | 116.98 | | | | | | |
| | | $Ni(NO_3)_2$—$5H_2O$ | 290.81 | 50 ml $H_2O$ | | | | | |
| | | $SnCl_2$ | 189.61 | 5 ml HCl | | | | | |

TABLE 4

| | | | | | | 380° C., 2.0% Butane/Air | | | |
| | | | | | | 1 sec | | 3 sec | |
| Composition $CoNi_wMo_xD_yO_{z'''}$ | Example | Salt Used | Gram Mole Weight | Solvent | Method of Synthesis | Conversion % | Selectivity % | Conversion % | Selectivity % |
| --- | --- | --- | --- | --- | --- | --- | --- | --- | --- |
| $Co_{0.5}Ni_{0.5}Mo_3Sn_{0.5}O_{z'''}$ | 22 | $Co(NO_3)_2$—$6H_2O$ | 291.03 | 20 ml $H_2O$ | freeze-dried | 12.5 | 32 | 29 | 27 |
| | | $SnCl_2$ | 189.61 | | | | | | |
| | | $(NH_4)_6Mo_7O_{24}$—$4H_2O$ | 1235.86 | 50 ml $H_2O$ | | | | | |
| | | $NiCl_2$—$6H_2O$ | 237.71 | 20 ml $HNO_3$ | | | | | |
| $Mo_3Co_{0.5}Ni_{0.5}Mn_1O_{z'''}$ | 23 | $Co(NO_3)_2$—$H_2O$ | 291.03 | 20 ml $H_2O$ | freeze-dried | 1.3 | 4 | 2.3 | 11 |
| | | $(CH_3CO_2)_2Mn$—$4H_2O$ | 245.09 | | | | | | |
| | | $(NH_4)_6Mo_7O_{24}$—$4H_2O$ | 1235.86 | 30 ml $H_2O$ | | | | | |
| | | $NiCl_2$—$6H_2O$ | 237.71 | 20 ml $H_2O$ | | | | | |
| $Mo_3Co_{0.5}Ni_{0.5}Ba_1O_{z'''}$ | 24 | $Co(NO_3)_2$—$6H_2O$ | 291.03 | 20 ml $H_2O$ | freeze-dried | 0.8 | 16 | 2.1 | 18 |
| | | $Ba(NO_3)_2$ | 261.34 | | | | | | |
| | | $(NH_4)_6Mo_7O_{24}$—$4H_2O$ | 1235.86 | 80 ml $H_2O$ | | | | | |
| | | $NiCl_2$—$6H_2O$ | 237.71 | 20 ml $H_2O$ | | | | | |
| $Mo_3Co_{0.5}Ni_{0.5}Al_1O_{z'''}$ | 25 | $Co(NO_3)_2$—$6H_2O$ | 291.03 | 20 ml $H_2O$ | freeze-dried | 3.9 | 15 | 10.5 | 8 |
| | | $Al(NO_3)_3$—$9H_2O$ | 375.13 | | | | | | |
| | | $(NH_4)_6Mo_7O_{24}$—$4H_2O$ | 1235.86 | 150 ml $H_2O$ | | | | | |
| | | $NiCl_2$—$6H_2O$ | 237.71 | 20 ml $H_2O$ | | | | | |
| $Mo_3Co_{0.5}Ni_{0.5}W_1O_{z'''}$ | 26 | $Co(NO_3)_2$—$6H_2O$ | 291.03 | 40 ml $H_2O$ | freeze-dried | 4.2 | 27 | 14.2 | 15 |
| | | $(NH_4)_{10}W_{12}O_{41}$—$5H_2O$ | 3132.64 | | | | | | |
| | | $(NH_4)_6Mo_7O_{24}$—$4H_2O$ | 1235.86 | 50 ml $H_2O$ | | | | | |
| | | $NiCl_2$—$6H_2O$ | 237.71 | 10 ml $H_2O$ | | | | | |

TABLE 5

| Composition $VNi_wCo_xMo_xE_yO_{z'''}$ | Example | Salt Used | Gram Mole Weight | Solvent | Method of Synthesis | 380° C., 2.0% Butane/Air | | | |
|---|---|---|---|---|---|---|---|---|---|
| | | | | | | 1 sec | | 3 sec | |
| | | | | | | Conversion % | Selectivity % | Conversion % | Selectivity % |
| $V_1Mo_{2.3}Ni_{0.5}Co_{0.5}$ $Fe_1O_{z''''}$ | 27 | $NH_4VO_3$ $(NH_4)_6Mo_7O_{24}$—$4H_2O$ $Co(OOCCH_3)_2$ $Ni(NO_3)_2$—$6H_2O$ $Fe(NO_3)_3$—$9H_2O$ | 116.98 1235.86 177.02 290.81 404 | 50 ml $H_2O$ 20 ml $H_2O$ 20 ml HCl 20 ml $H_2O$ | freeze-dried | 15 | 13 | 32 | 7 |
| $V_1Mo_{2.3}Ni_{0.5}Co_{0.5}$ $Ca_1O_{z''''}$ | 28 | $NH_4VO_3$ $(NH_4)_6Mo_7O_{24}$—$4H_2O$ $Co(OOCCH_3)_2$ $Ni(NO_3)_2$—$6H_2O$ $Ca(NO_3)_2$—$4H_2O$ | 116.98 1235.86 177.02 290.81 236.15 | 50 ml $H_2O$ 20 ml HCl 5 ml HCl | freeze-dried | 14 | 10 | 34 | 4 |
| $V_1Mo_{2.3}Co_{0.5}Ni_{0.5}$ $Mn_1O_{z''''}$ | 29 | $NH_4VO_3$ $(NH_4)_6Mo_7O_{24}$—$4H_2O$ $Co(OOCCH_3)_2$ $Ni(NO_3)_2$—$6H_2O$ $(CH_3CO_2)_2Mn$—$4H_2O$ | 116.98 1235.86 177.02 290.81 245.09 | 50 ml $H_2O$ 20 ml $H_2O$ 20 ml HCl 10 ml $H_2O$ | freeze-dried | 12.5 | 2.5 | 29.2 | 1 |
| $V_1Mo_{2.3}Co_{0.5}Ni_{0.5}$ $Sr_1O_{z''''}$ | 30 | $NH_4VO_3$ $(NH_4)_6Mo_7O_{24}$—$4H_2O$ $Co(OOCCH_3)_2$ $Ni(NO_3)_2$—$6H_2O$ $Sr(NO_3)_2$ | 116.98 1235.86 177.02 290.81 211.63 | 50 ml $H_2O$ 20 ml HCl 10 ml $H_2O$ | freeze-dried | 21 | 17 | 47 | 10 |
| $V_1Mo_{2.3}Co_{0.5}Ni_{0.5}$ $Eu_1O_{z''''}$ | 31 | $NH_4VO_3$ $(NH_4)_6Mo_7O_{24}$—$_{4H2O}$ $Co(OOCCH_3)_2$ $Ni(NO_3)_2$—$6H_2O$ $EuCl_2$ | 116.98 1235.86 177.02 290.81 222.87 | 50 ml $H_2O$ 20 ml HCl 10 ml $H_2O$ | freeze-dried | 24 | 7.5 | 54 | 2 |
| $V_1Mo_{2.3}Co_{0.5}Ni_{0.5}$ $La_1O_{z''''}$ | 32 | $NH_4VO_3$ $(NH_4)_6Mo_7O_{24}$—$4H_2O$ $Co(OOCCH_3)_2$ $Ni(NO_3)_2$—$6H_2O$ $La(NO_3)_3$—$5H_2O$ | 116.98 1235.86 177.02 290.81 415.01 | 50 ml $H_2O$ 20 ml HCl 10 ml $H_2O$ | freeze-dried | 17 | 10 | 36 | 5 |
| $V_1Mo_{2.3}Co_{0.5}Ni_{0.5}$ $Zr_1O_{z''''}$ | 33 | $NH_4VO_3$ $(NH_4)_6Mo_7O_{24}$—$4H_2O$ $Co(OOCCH_3)_2$ $Ni(NO_3)_2$—$6H_2O$ $Zr(SO_4)_2$—$4H_2O$ | 116.98 1235.86 177.02 290.81 355.32 | 50 ml $H_2O$ 20 ml HCl 40 ml $H_2O$ | freeze-dried | 20 | 17.5 | 46 | 12 |
| $V_1Mo_{2.3}Co_{0.5}Ni_{0.5}$ $Ga_1O_{z''''}$ | 34 | $NH_4VO_3$ $(NH_4)_6Mo_7O_{24}$—$4H_2O$ $Co(OOCCH_3)_2$ $Ni(NO_3)_2$—$6H_2O$ $Ga(NO_3)_3$ | 116.98 1235.86 177.02 290.81 255.74 | 50 ml $H_2O$ 20 ml HCl | freeze-dried | 18 | 16.5 | 43 | 11 |
| $V_1Mo_{2.3}Co_{0.5}Ni_{0.5}$ $Pb_1O_{z''''}$ | 35 | $NH_4VO_3$ $(NH_4)_6Mo_7O_{24}$—$4H_2O$ $Co(OOCCH_3)_2$ $Ni(NO_3)_2$—$6H_2O$ $Pb(NO_3)_2$ | 116.98 1235.86 177.02 290.81 331.2 | 50 ml $H_2O$ 20 ml HCl 100 ml HCl 86 ml $NH_4OH$ | freeze-dried (with dry ice and acetone) | 22 | 20 | 47 | 14 |

TABLE 6

| Composition | Example | Salt Used | Gram Mole Weight | Solvent | Method of Synthesis | 380° C., 2.0% Butane/Air | | | |
|---|---|---|---|---|---|---|---|---|---|
| | | | | | | 1 sec | | 3 sec | |
| | | | | | | Conversion % | Selectivity % | Conversion % | Selectivity % |
| $V2Mo_1Ox$ | 36 | $V_2O_5$ 90.94 g $MoO_3$ 71.97 g | 181.88 143.94 | 1034 ml isobutyl alcohol 95 ml benzyl alcohol | Alcohol reflux | 60 | 10 | 90 | 0 |

TABLE 7

| | | | | | | 380° C., 2.0% Butane/Air | | | |
|---|---|---|---|---|---|---|---|---|---|
| | | | | | | 1 sec | | 3 sec | |
| Composition | Comp. Example | Salt Used | Gram Mole Weight | Solvent | Method of Synthesis | Conversion % | Selectivity % | Conversion % | Selectivity % |
| $MoO_3$ | 37 | $(NH_4)_6Mo_7O_{24}$—$4H_2O$ | 1235.9 | | freeze-dried | 11 | <1 | | |
| VPO | 38 | $NH_4VO_3$ $H_3PO_4$ | 116.965 97.97 | | freeze-dried | 8 | 20 | | |
| $Ni_1W_{2.3}O_t$ | 39 | $H_2WO_4$ $NiCl_2$—$6H_2O$ | 249.86 237.71 | 50 ml $H_2O$ 180 ml $NH_4OH$ | freeze-dried | 2.5 | 0 | 9 | 0 |
| $Ni_1Mo_{2.3}P_1O_t$ | 40 | $Ni(NO_3)_2$ $(NH_4)_6Mo_7O_{24}$—$4H_2O$ $H_3PO_4$ | 290.8 1235.86 98 | 50 ml $H_2O$ 100 ml $H_2O$ | freeze-dried | 6 | 12 | | |
| $V_2O_5$ | 41 | | | | freeze-dried | 80 | <1 | | |

What is claimed is:

1. A process for the preparation of a molybdenum compound comprising a molybdenum compound of formula I, II, III, IV or V:

I $V_qMoA_yO_z$
II $NiMo_xB_yO_{z'}$
III $VNi_wMo_xC_yO_{z''}$
IV $CoNi_wMo_xD_yO_{z'''}$
V $VNi_wCo_rMo_xE_yO_{z''''}$ wherein:
   q is a number from 0.1 to 10;
   r is a number from 0.1 to 10;
   w is a number from 0.1 to 10;
   x is a number from 0.1 to 10;
   y is a number from 0.1 to 10;
   y' is a number from 0 to 10,
   A is at least one cation selected from the group consisting of cations of: Cr, Ce and Pb;
   B is at least one cation selected from the group consisting of cations of: Al and W;
   C is at least one cation selected from the group consisting of cations of: Fe, Zn, Al, Sb, Bi, W, Li, Ba, Nb and Sn;
   D is at least one cation selected from the group consisting of cations of: Ba, Mn, Al, Sb, Sn, and W;
   E is at least one cation selected from the group consisting of cations of: Fe, Ca, Mn, Sr, Eu, La, Zr, Ga, Sn and Pb; and
   z, z', z", z''', and z"" are determined using the amounts and oxidation states of all cations present in each formula according to the following equations:

z=((q times oxidation state of V)+(1 times oxidation state of Mo)+(y times oxidation state of A)) divided by 2 (oxidation state of oxygen);

z'=((1 times oxidation state of Ni)+(x times oxidation state of Mo)+(y times oxidation state of B)) divided by 2 (oxidation state of oxygen);

z"=((1 times oxidation state of V)+(w times the oxidation state of Ni)+(x times oxidation state of Mo)+(y' times oxidation state of C)) divided by 2 (oxidation state of oxygen);

z'''=((1 times oxidation state of Co)+(w times the oxidation state of Ni)+(x times oxidation state of Mo)+(y' times oxidation state of D)) divided by 2 (oxidation state of oxygen); and z""=((1 times oxidation state of V)+(w times the oxidation state of Ni)+(r times the oxidation state of Co)+(x times oxidation state of Mo)+(y' times oxidation state of E)) divided by 2 (oxidation state of oxygen), comprising the steps of:

contacting at least one compound having a cation of the molybdenum with at least one cation containing compound for each of the other cations of the molybdenum compound in a solution comprising water to form a resultant solution or colloid;

freezing the resultant solution or colloid to form a frozen material;

freeze drying the frozen material; and heating the dried frozen material to yield the molybdenum compound of formula I, II, III, IV, or V.

* * * * *